(12) United States Patent
Bocek et al.

(10) Patent No.: US 10,016,593 B2
(45) Date of Patent: Jul. 10, 2018

(54) IMPLANTABLE MEDICAL DEVICE HAVING ELECTROMAGNETIC INTERFERENCE FILTER DEVICE TO REDUCE POCKET TISSUE HEATING

(71) Applicant: Boston Scientific Neuromodulation Corporation, Valencia, CA (US)

(72) Inventors: Joseph Bocek, Seattle, WA (US); Kiran Gururaj, Valencia, CA (US); Matthew McDonald, Pasadena, CA (US); Gaurav Gupta, Valencia, CA (US); Mizanur Rahman, Valencia, CA (US); Ross Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 43 days.

(21) Appl. No.: 15/229,110

(22) Filed: Aug. 4, 2016

(65) Prior Publication Data

US 2016/0339236 A1 Nov. 24, 2016

Related U.S. Application Data

(63) Continuation of application No. 14/094,428, filed on Dec. 2, 2013, now Pat. No. 9,433,782.
(Continued)

(51) Int. Cl.
*A61N 1/00* (2006.01)
*A61N 1/08* (2006.01)
(Continued)

(52) U.S. Cl.
CPC ............. *A61N 1/08* (2013.01); *A61N 1/0551* (2013.01); *A61N 1/3605* (2013.01);
(Continued)

(58) Field of Classification Search
CPC .......... A61N 1/36125; A61N 2001/086; A61N 1/375
(Continued)

(56) References Cited

U.S. PATENT DOCUMENTS 5,649,965 A 7/1997 Pons et al.
6,198,972 B1 3/2001 Hartlaub et al.
(Continued)

OTHER PUBLICATIONS

PCT International Search Report for PCT/US2013/072665 dated Apr. 3, 2014 (4 pages).
(Continued)

*Primary Examiner* — Amanda Patton
*Assistant Examiner* — Philip C Edwards
(74) *Attorney, Agent, or Firm* — Lowe Graham Jones PLLC; Bruce E. Black (57) ABSTRACT

An active implantable medical device (AIMD) for use with a medical lead carrying at least one lead electrode. The AIMD comprises interior electronic circuitry configured for performing a medical function via the medical lead, an electrically conductive case containing the interior electronic circuitry, at least one electrical terminal configured for electrically coupling the electronic circuitry respectively to the lead electrode(s), and an inductive element coupled in series between the electrical terminal(s) and the case. The inductive element is configured for hindering the shunting of electrical current from the at least one electrical terminal to the case that has been induced by electromagnetic interference (EMI) impinging on the medical lead.

20 Claims, 5 Drawing Sheets

Related U.S. Application Data (60) Provisional application No. 61/733,347, filed on Dec. 4, 2012.

(51) Int. Cl.
*A61N 1/37* (2006.01)
*A61N 1/36* (2006.01)
*A61N 1/05* (2006.01)

(52) U.S. Cl.
CPC .............. *A61N 1/3718* (2013.01); *A61N 1/05* (2013.01); *A61N 1/086* (2017.08)

(58) Field of Classification Search
USPC ........................................................ 607/116
See application file for complete search history.

(56) References Cited

U.S. PATENT DOCUMENTS

| | | |
|---|---|---|
| 6,209,764 B1 | 4/2001 | Hartlaub et al. |
| 6,901,292 B2 | 5/2005 | Hrdlicka et al. |
| 7,164,950 B2 | 1/2007 | Kroll et al. |
| 7,650,184 B2 | 1/2010 | Walter |
| 7,729,770 B2 | 7/2010 | Stevenson et al. |
| 7,751,903 B2 | 7/2010 | Stevenson et al. |
| 8,019,439 B2 | 9/2011 | Kuzma et al. |
| 8,103,347 B2 | 1/2012 | Erickson |
| 2004/0199069 A1 | 10/2004 | Connelly et al. |
| 2005/0197677 A1 | 9/2005 | Stevenson |
| 2007/0123949 A1 | 5/2007 | Dabney et al. |
| 2007/0150036 A1 | 6/2007 | Anderson |
| 2007/0168004 A1 | 7/2007 | Walter |
| 2007/0168007 A1 | 7/2007 | Kuzma et al. |
| 2011/0106217 A1 | 5/2011 | Stancer et al. |
| 2012/0253340 A1* | 10/2012 | Stevenson ................ A61N 1/05 606/33 |
| 2012/0265045 A1 | 10/2012 | Stevenson et al. |

OTHER PUBLICATIONS

PCT Written Opinion of the International Search Authority for PCT/US2013/072665 dated Apr. 3, 2014 (3 pages).
Official Communication for U.S. Appl. No. 14/094,428 dated Mar. 20, 2015.
Official Communication for U.S. Appl. No. 14/094,428 dated Sep. 15, 2015.
Official Communication for U.S. Appl. No. 14/094,428 dated Feb. 8, 2015.

\* cited by examiner

IMPLANTABLE MEDICAL DEVICE HAVING ELECTROMAGNETIC INTERFERENCE FILTER DEVICE TO REDUCE POCKET TISSUE HEATING

RELATED APPLICATION DATA

The present application is a continuation of U.S. patent application Ser. No. 14/094,428 filed Dec. 2, 2013 which claims the benefit under 35 U.S.C. § 119 to U.S. Provisional Application No. 61/733,347, filed Dec. 4, 2012, both of which are hereby incorporated by reference into the present application in their entirety.

FIELD OF THE INVENTION

The present invention relates to implantable medical devices, and in particular, techniques for preventing heating of the tissue pocket surrounding an implantable medical device in the presence of Magnetic Resonance Imaging.

BACKGROUND OF THE INVENTION

Active implantable medical devices (AIMDs) find applicability in neurostimulation systems that deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. AIMDs are typically implanted within a tissue pocket of the patient, and connected to neurostimulation leads that are implanted at a target stimulation site remote from the tissue pocket.

AIMDs that are used in neurostimulation systems take the form of two general types: fully implanted and radio-frequency (RF)-controlled. The fully implanted AIMD contains the control circuitry, as well as a power supply, e.g., a battery, all within an implantable pulse generator (IPG) connected to one or more leads with one or more electrodes for stimulating tissue, so that once programmed and turned on, the IPG can operate independently of external hardware. The IPG is turned on and off and programmed to generate the desired stimulation pulses from an external programming device using transcutaneous electromagnetic links. In contrast, the RF-controlled AIMD includes an external transmitter inductively coupled via an electromagnetic link to an implanted receiver-stimulator connected to one or more leads with one or more electrodes for stimulating tissue. The power source, e.g., a battery, for powering the implanted receiver, as well as control circuitry to command the receiver-stimulator, is contained in the external controller—a hand-held sized device typically worn on the patient's belt or carried in a pocket. Data/power signals are transcutaneously coupled from a cable-connected transmission coil placed over the implanted receiver-stimulator. The implanted receiver-stimulator receives the signal and generates the stimulation.

AIMDs typically incorporate a sealing enclosure or case (commonly referred to as a "can") that contacts tissue when implanted within the patient. This enclosure is constructed from a biocompatible material, and typically a metallic material, such as titanium. The interior components contained within the case are typically electronic circuits designed for processes, such as physiological signal sensing, diagnosis, data storage, therapy delivery, and telemetry. The case serves to isolate the interior components, which are typically not biocompatible, from the biological environment. In some AIMDs, the case also serves as a common or return electrode that allows sensing and delivery of stimulation energy. This practice is commonly referred to as "monopolar" or "unipolar" sensing or therapy.

AIMDs are routinely implanted in patients who are in need of Magnetic Resonance Imaging (MRI). Thus, when designing implantable neurostimulation systems, consideration must be given to the possibility that the patient in which AIMD is implanted may be subjected to EMI generated by MRI scanners, which may potentially cause damage to the AIMD, as well as discomfort to the patient. In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the presence of a large static magnetic field. Present-day MRI scanners can have maximum gradient strengths of 100 mT/m and fast switching times (slew rates) of 150 mT/m/ms, which can result in induced voltages with frequency content comparable to stimulation therapy frequencies. Typical MRI scanners create gradient fields in the range of 100 Hz to 30 KHz, and Radio Frequency (RF) fields of 64 MHz for a 1.5 Tesla scanner and 128 MHz for a 3 Tesla scanner.

To a certain extent, the AIMD case provides protection against electromagnetic interference (EMI) from environmental sources and medical diagnostic tools, such as MRI scanners. However, the strength of the gradient magnetic field may be high enough to induce voltages (5-10 Volts depending on the orientation of the lead inside the body with respect to the MRI scanner) on to the stimulation lead(s), which in turn, are seen by the AIMD electronics. If these induced voltages are higher than the voltage supply rails of the AIMD electronics, there could exist paths within the AIMD that could induce current through the electrodes on the stimulation lead(s), which in turn, could cause unwanted stimulation to the patient due to the similar frequency band, between the MRI-generated gradient field and intended stimulation energy frequencies for therapy, as well as potentially damaging the electronics within the AIMD. To elaborate further, the gradient (magnetic) field may induce electrical energy within the wires of the stimulation lead(s), which may be conveyed into the circuitry of the AIMD and then out to the electrodes of the stimulation leads via the passive charge recovery switches. For example, in a conventional neurostimulation system, an induced voltage at the connector of the AIMD that is higher than AIMD battery voltage (~4-5V), may induce such unwanted stimulation currents. RF energy generated by the MRI scanner may induce electrical currents of even higher voltages within the AIMD.

In some embodiments, the induced RF electrical current is shunted to the AIMD case to protect AIMD internal components. However, the induced electrical current may be collected in an additive fashion, and result in significant RF current flow from the AIMD case into the tissue pocket surrounding the AIMD case. This, in turn, results in heating of the tissue, with the potential for patient discomfort or even tissue damage. For neurostimulation systems that use more than one lead electrode connection in the AIMD, the amount of impinging RF current from the leads may increase as the number of lead electrodes increases, provided that the RF current arrives at the AIMD with similar phases from the various lead electrodes. This potentially exacerbates this heating phenomenon for implanted neurostimulation systems with a large number of lead electrodes (e.g., multi-lead AIMDs having eight or more electrodes per lead).

There, thus, remains a need to prevent RF current from being conveyed to the case electrically connected to the internal electronics contained within an AIMD.

SUMMARY OF THE INVENTION

In accordance with the present inventions, an active implantable medical device (AIMD) for use with a medical lead carrying at least one lead electrode is provided. The AIMD comprises interior electronic circuitry configured for performing a medical function (e.g., the conveyance of electrical stimulation energy and/or sensing of a physiological parameter) via the medical lead. The AIMD further comprises an electrically conductive case containing the interior electronic circuitry. The AIMD further comprises at least one electrical terminal configured for electrically coupling the electronic circuitry respectively to the lead electrode(s). The AIMD further comprises an inductive element coupled in series between the at least one electrical terminal and the case. The inductive element is configured for hindering, and preferably preventing, the shunting of electrical current from the terminal(s) to the case that has been induced by electromagnetic interference (EMI) impinging on the medical lead.

In one embodiment, the inductive element is electrically coupled in series between the interior electronic circuitry and one of the electrical terminal(s) and the case, and the interior electronic circuitry is configured to operate at a frequency below the frequency of the induced electrical current, thereby allowing electrical current to be conveyed between the at least one electrical terminal and the interior electronic circuitry. In one embodiment, the operating frequency of the interior electronic circuitry may be below 100 KHz, and the frequency of the induced electrical current is above 1 MHz. In another embodiment, the operating frequency of the interior electronic circuitry may be below 1 KHz, and the frequency of the induced electrical current is at least 64 MHz.

The AIMD further comprises at least one capacitive element electrically coupled respectively in series between the electrical terminal(s) and a common terminal, and another capacitive element electrically coupled in series between the case and the common terminal, thereby electrically isolating the electrical terminal(s) and case from each other at the operating frequency. The AIMD may optionally comprise a connector configured for removably connecting the lead to the at least one electrical terminal.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
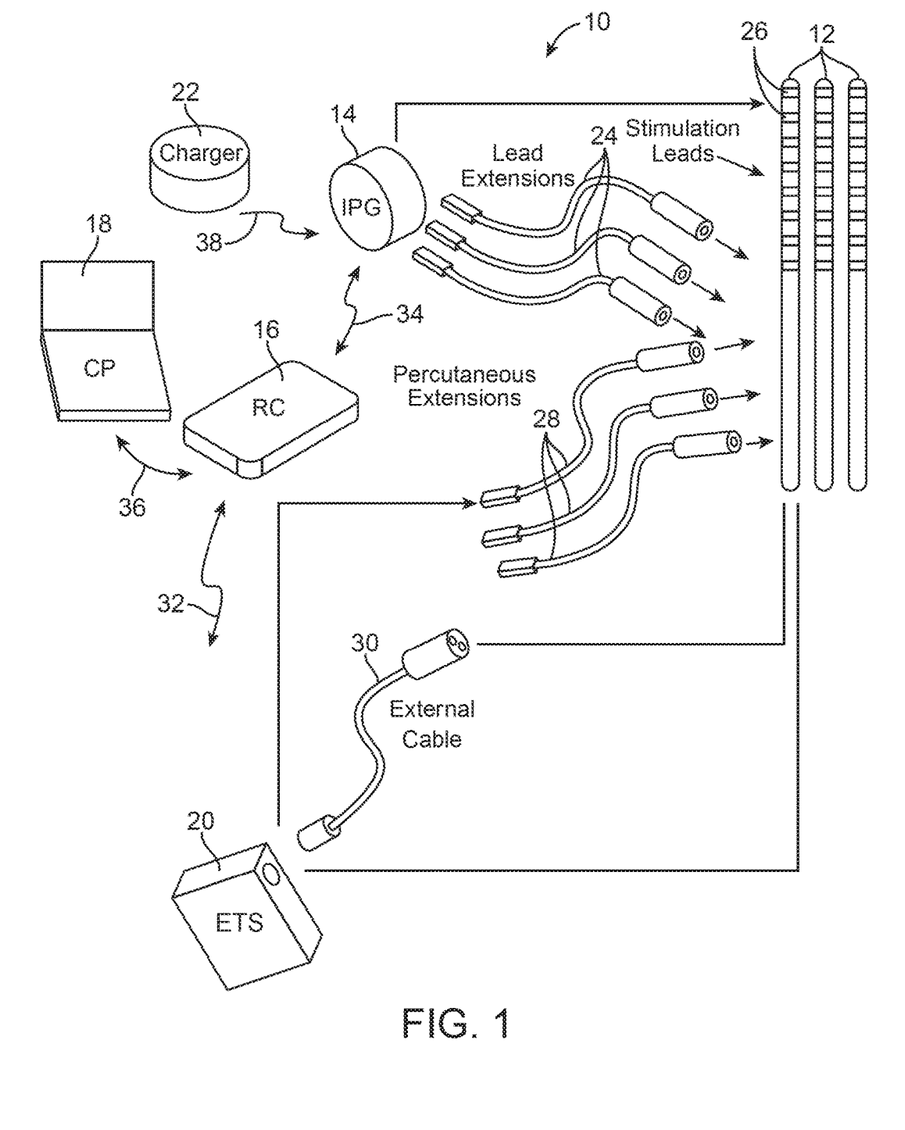
FIG. 1 is a plan view of a Spinal Cord Stimulation (SCS) system constructed in accordance with one embodiment of the present inventions.

Turning first to FIG. 1, an exemplary spinal cord stimulation (SCS) system 10 generally includes one or more (in this case, three) implantable stimulation leads 12, an active implantable medical device (AIMD), and in particular, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
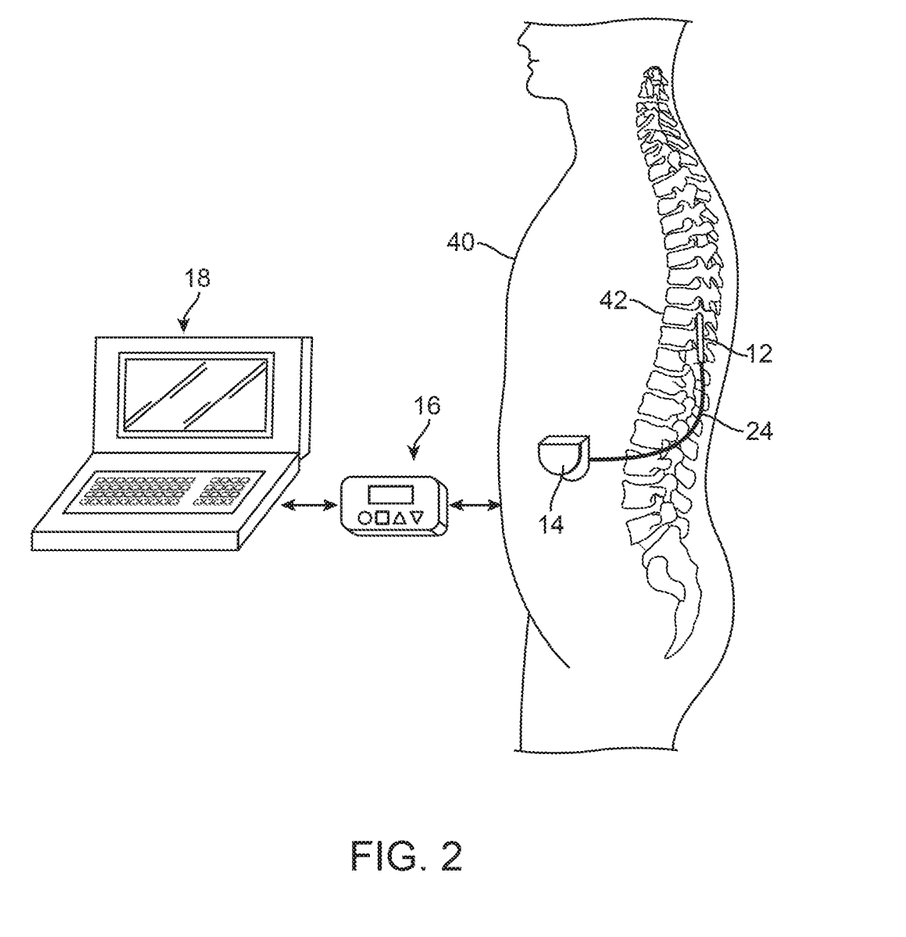
FIG. 2 is a plan view of the SCS system of FIG. 1 in use within a patient.

As shown in FIG. 2, the stimulation leads 12 are implanted within the spinal column 42 of a patient 40. The preferred placement of the stimulation leads 12 is adjacent, i.e., resting near, the spinal cord area to be stimulated. Due to the lack of space near the location where the stimulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16.

Figure 3:
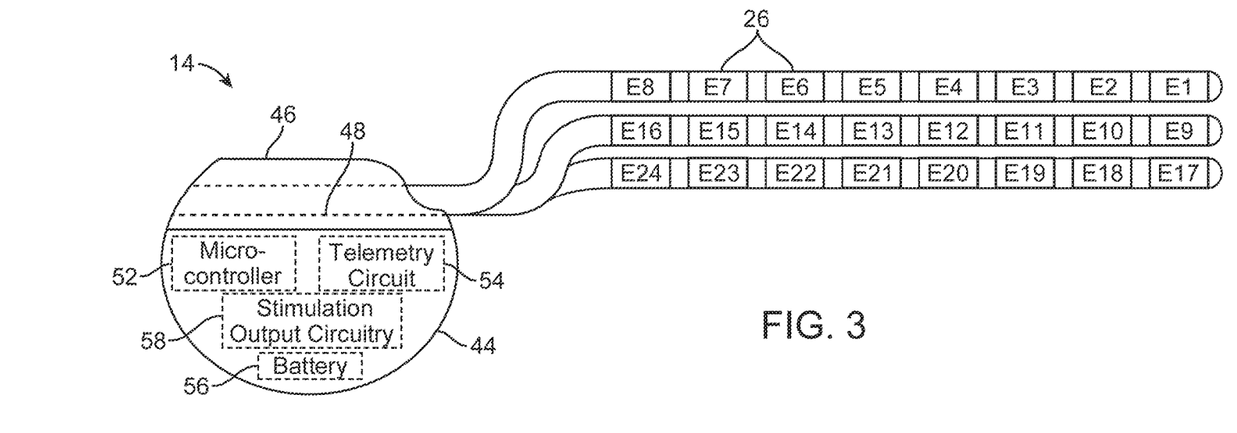
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Stimulation lead for Neural Stimulation and Method of Making Same," the disclosures of which are expressly incorporated herein by reference.

Figure 4:
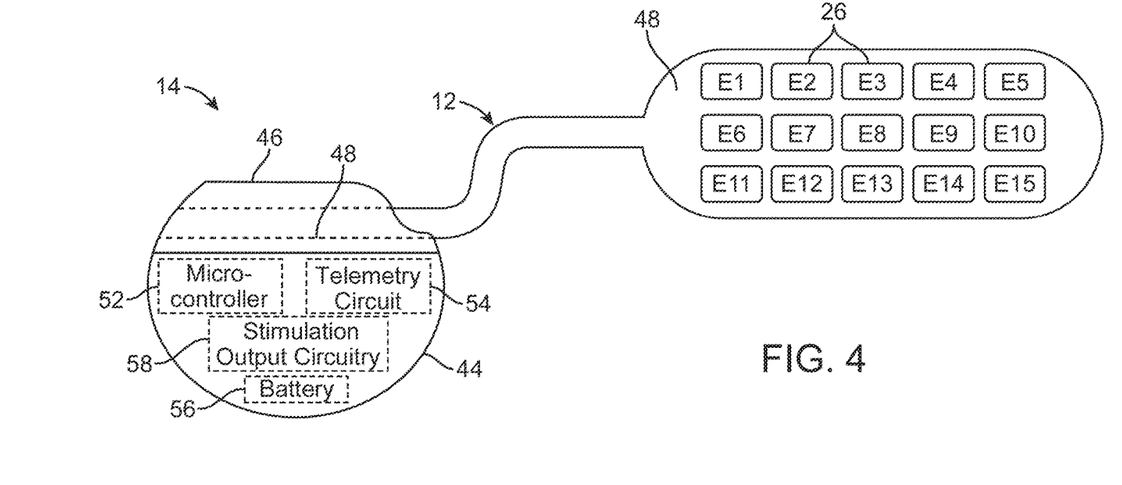
FIG. 4 is a plan view of an implantable pulse generator (IPG) and a surgical paddle lead used in the SCS system of FIG. 2.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for case the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the stimulation lead(s) 12. In the case where the lead extensions 24 are used, the port(s) 48 may instead receive the proximal ends of such lead extensions 24.

The IPG 14 further comprises interior electronic circuitry, such as a microcontroller 52, a telemetry circuit 54, a battery 56, stimulation output circuitry 58, and other suitable components known to those skilled in the art. The microcontroller 52 executes a suitable program stored in memory (not shown), for directing and controlling the electrical stimulation therapy performed by IPG 14. The telemetry circuit 54 (including antenna is configured for receiving programming data (e.g., the operating program and/or neurostimulation parameters) from the RC 16 in an appropriate modulated carrier signal, and demodulating the carrier signal to recover the programming data, which programming data is then stored in memory. The battery 56, which may be a rechargeable lithium-ion or lithium-ion polymer battery, provides operating power to IPG 14.

The stimulation output circuitry 58 that provides electrical stimulation energy in the form of a pulsed electrical waveform to the electrode array 26 in accordance with a set of stimulation parameters programmed into the IPG 14. In the illustrated embodiment, the stimulation output circuitry 58 may either comprise independently controlled current sources for providing stimulation pulses of a specified and known amperage to or from the electrodes 26 or case 44, or independently controlled voltage sources for providing stimulation pulses of a specified and known voltage at the electrodes 26. The stimulation output circuitry 58 may further include charge recovery circuitry (not shown) to provide charge balancing of the electrodes and recovery of charge from the tissue. The interior electronic circuitry may include circuitry capable of performing medical functions other than generating and delivering electrical stimulation energy to tissue. For example, the interior electronic circuitry may include monitoring circuitry (not shown) for measuring electrical parameter data (e.g., electrode impedance and/or electrode field potential).

The stimulation parameters in accordance with which the stimulation output circuitry 58 generates the pulsed electrical waveform to the electrode array 26 may, e.g., comprise electrode combinations, which define the electrodes that are activated as anodes (positive), cathodes (negative), and turned off (zero), percentage of stimulation energy assigned to each electrode of the array of electrodes 26 (fractionalized electrode configurations), and electrical pulse parameters, which define the pulse amplitude (measured in milliamps or volts depending on whether the IPG 14 supplies constant current or constant voltage to the array of electrodes 26), pulse width (measured in microseconds), pulse rate (measured in pulses per second), and burst rate (measured as the modulation on duration X and modulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Significant to the present inventions, electrical current induced by electromagnetic interference (EMI) impinging on the stimulation leads 12 is prevented, or at the least hindered, from being shunted to the outer case 44 of the IPG 14, while the pulsed electrical stimulation current is allowed to be conveyed between the interior electronic circuitry of the IPG 14 and the stimulation leads 12 and outer case 44. In this manner, any heating of the case 44 due to the induction of electrical current on the lead electrodes 26 by the EMI is eliminated or reduced, thereby eliminating or reducing the heating of tissue surrounding the IPG that may otherwise occur.

Figure 5:
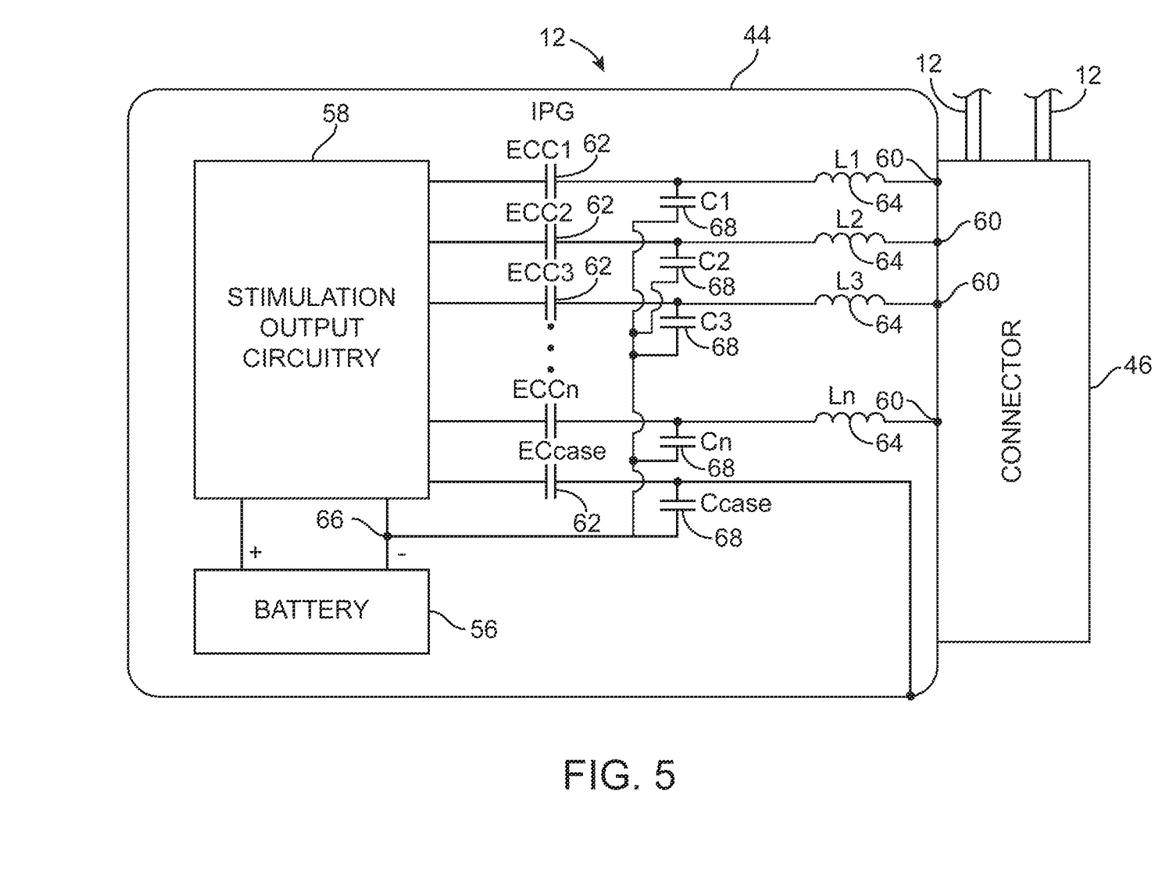
FIG. 5 is a block diagram of one filter arrangement that can be used in the IPG to prevent shunting of electrical current to the IPG case.

In particular, and with reference to FIG. 5, the stimulation output circuitry 58 is electrically coupled to electrical terminals 60, which when the stimulation leads 12 are mated with the connector 46, are in turn electrically coupled to the corresponding electrodes 26 carried by the leads 12. The stimulation output circuitry 58 is also electrically coupled to the case 44. As briefly discussed above, the stimulation output circuitry 58 may generate and convey pulsed electrical energy between selected lead electrodes 26 in a bipolar or tripolar manner, or may generate and convey the pulsed electrical energy between selected lead electrodes 26 and the case 44 in a monopolar manner. Direct current (DC) blocking capacitors 62 (ECC1-ECcase) are provided between the stimulation output circuitry 58 and the electrical terminals 60 and case 44 to minimize electrical charge build up in the tissue.

Figure 6:
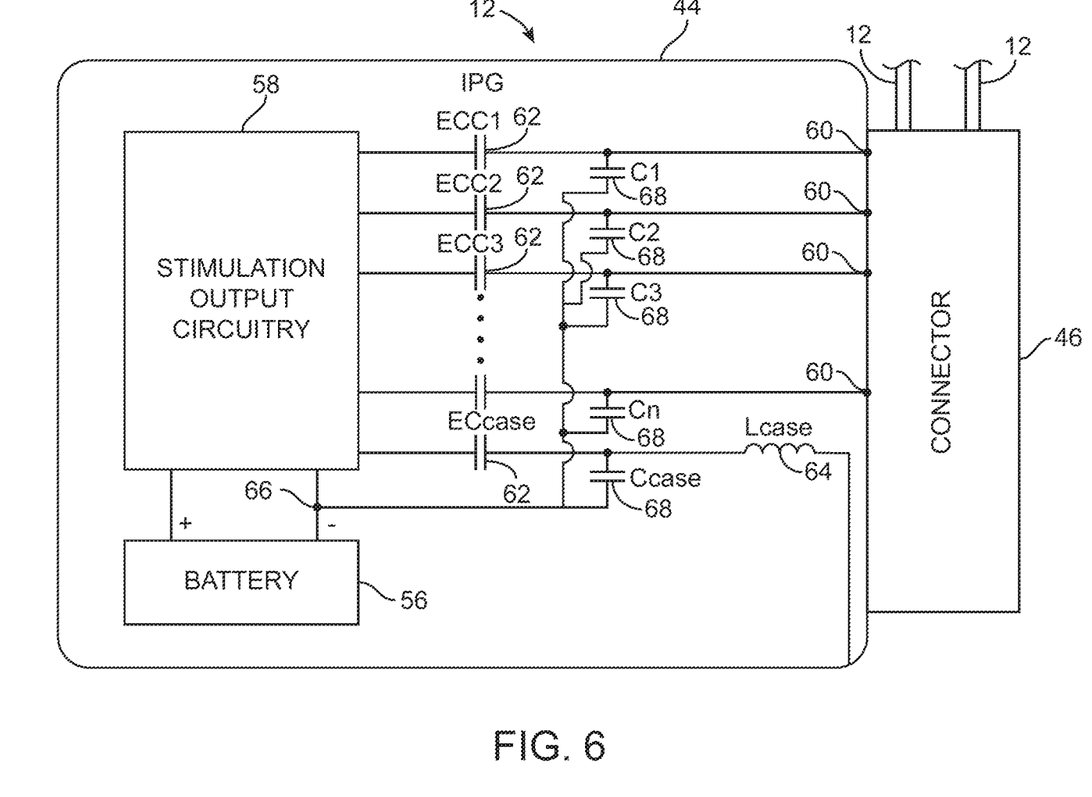
FIG. 6 is a block diagram of one filter arrangement that can be used in the IPG to prevent shunting of electrical current to the IPG case.

Significantly, the inductive elements 64 (L1-Ln) are coupled in series (from the perspective of the electrical current induced on the lead electrodes 26 as an electrical source and the potential electrical path created between the lead electrodes 26 and the case 44) between the respective electrical terminals 60 and the case 44. In the embodiment illustrated in FIG. 5, the inductive elements 64 are also electrically coupled between the stimulation output circuitry 58 and the respective electrical terminals 60. In an alternative embodiment illustrated in FIG. 6, an inductive element 64 ($L_{case}$) is electrically coupled between the stimulation output circuitry 58 and the case 44. Capacitive elements 68 (C1-$C_{case}$) are coupled in series between the electrical terminals 60 and case 44 and a common (ground) terminal 66 of the stimulation output circuitry 58. These capacitive elements 68 are selected to have sufficiently low capacitive value to have a high impedance at frequencies of the electrical stimulation energy generated by the stimulation output circuitry 58, thereby electrically isolating the electrical terminals 60 and the case 44 from each other at these operating frequencies. In a particular embodiment, the impedance of the capacitive elements 68 at the highest frequency of electrical stimulation energy is selected to be at least ten times higher than the tissue impedance at this frequency (e.g., 500 pf-2000 pf). Although the capacitive elements 68 are shown in FIGS. 5 and 6 as being respectively coupled between the inductive elements 64 and the DC blocking capacitors 62, the capacitive elements 68 may be coupled between the respective DC blocking capacitors 62 and the stimulation output circuitry 58.

Because the frequency of the electrical stimulation energy generated by the stimulation output circuitry 58 is substantially lower than the expected frequency of the electrical current induced on the electrical terminals 60 by EMI impinging on the stimulation leads 12, the shunting of EMI-induced electrical current to the case 44 is hindered, while the conveyance of the electrical stimulation energy conveyed between the stimulation output circuitry 58 and the electrical terminals 60, or alternatively the electrical stimulation energy conveyed between the case 44 and the stimulation output circuitry 58, is allowed. For example, it is expected that the frequency of the electrical stimulation energy will be below 100 KHz, while it is expected that the frequency of the EMI-induced electrical current will be above 1 MHz, and in the case of EMI generated by an MRI scanner, at least 64 MHz (64 MHz for a 1.5 Tesla scanner and 128 MHz for a 3 Tesla scanner).

Thus, the inductance value of each of the inductive elements 64 has a relatively low impedance compared to the impedance presented by the lead and tissue at the operating frequencies of IPG 14 (i.e., the frequency of the electrical stimulation energy generated by the stimulation output circuitry 58 or the frequency of the electrical energy sensed by the monitoring circuitry (not shown)), allowing signals to pass between the internal electronic circuitry and the electrical terminals 58 and/or case 44, while the inductance value has a relatively high impedance compared to the RF output impedance of the lead at the IPG-connected contacts at the EMI frequencies, which is typically in the 30 to 150 ohm range. In the case where different EMI frequencies must be taken into account, each of the inductive elements 64 should maintain a high impedance for this range of EMI frequencies.

Based on these frequency parameters, the inductance values of the inductive elements 64 can be appropriately selected. For example, in the embodiment illustrated in FIG. 5, the inductance value of each inductive element 64 may be equal to at least 0.5 µH, preferably equal to at least 1.0 µH, and most preferably equal to at least 3.0 µH. In the case of a 1.5T MRI scanner that operates at 64 MHz, a 0.5 µH inductor will have an impedance of 200 ohms, a 1.0 µH inductor will have an impedance of 400 ohms, and a 3.0 µH inductor will have an impedance of 1200 ohms. In the embodiment illustrated in FIG. 6, the inductance value of the inductive element 64 may be in the range of 50 nH to 200 nH. In the case of a 1.5T MRI scanner that operates at 64 MHz, an inductor in the range of 50 nH to 200 nH will have an impedance in the range of 20-80 ohms. Ultimately, to effectively preventing heating of the tissue that would otherwise occur by shunting the induced current to the case 44, the impedance of each inductive element 64 should maintain a high impedance relative to the stimulation leads 12 and the casing-to-tissue impedance. The effective lead impedance may be the parallel combination of impedances measured from the lead electrodes 26 and case 44 back into the stimulation leads 12 at the EMI frequencies, as this is the effective impedance when the lead electrodes 26 and case 44 are connected in parallel through the inductive elements 64.

The inductive elements 64 preferably do not have any core materials that are subject to magnetic saturation when exposed to strong static magnetic fields (e.g., the static magnetic fields emitted by conventional MRI scanners), such that inductive elements 64 maintains a high impedance at the EMI frequencies. Preferably, each inductive element 64 has a sufficiently high self-resonant frequency to maintain adequate impedance at the EMI frequencies.

Notably, the embodiments illustrated in FIGS. 5 and 6 may have certain advantages relative to each other. In particular, with respect to the FIG. 5 embodiment, in addition to preventing or hindering the electrical current induced on the lead electrodes 26 from being conveyed to the case 44, the inductive elements 64 (L1-Ln) also reduces the common mode RF voltage levels with respect to the case 44, thereby preventing or hinders the induced electrical current from being conveyed to the stimulation output circuitry 58 in the form of injected power, while the pulsed electrical stimulation current is allowed to be conveyed between the interior electronic circuitry of the IPG 14 and the stimulation leads 12 and outer case 44. This could be advantageous to keep electrical current low to the case 44 if there is a high stray capacitance from the stimulation output circuitry 58 to the case 44. With respect to the FIG. 6 embodiment, the use of only the inductive element 64 ($L_{case}$) minimizes the component count relative to the FIG. 5 embodiment, which uses an inductive element 64 for each lead electrode 26.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An active implantable medical device (AMID) for use with a medical lead carrying at least one lead electrode, comprising:
   interior electronic circuitry configured for performing a medical function via the medical lead;
   an electrically conductive case containing the interior electronic circuitry;
   at least one electrical terminal configured for electrically coupling the interior electronic circuitry respectively to the least one lead electrode;
   a plurality of DC blocking capacitors, wherein one of the DC blocking capacitors is coupled in series between each of the at least one electrical terminal and the interior electronic circuitry and one of the DC blocking capacitors is coupled in series between the case and the interior electronic circuitry;
   at least one capacitive element electrically coupled in series between each of the at least one electrical terminal and a common terminal; and
   another capacitive element electrically coupled in series between the case and the common terminal.

2. The AIMD of claim 1, wherein the interior electronic circuitry is configured for conveying electrical stimulation energy between the at least one electrical terminal and the case.

3. The AIMD of claim 1, wherein the interior electronic circuitry is configured for sensing a physiological parameter between the at least one electrical terminal and the case.

4. The AIMD of claim 1, further comprising a connector configured for removably connecting the lead to the at least one electrical terminal.

5. The AMID of claim 1, wherein an operating frequency of the interior electronic circuitry is below 100 KHz.

6. The AIMD of claim 1, further comprising an inductive element disposed within the case and coupled in series between the at least one electrical terminal and the case, the inductive element being configured for hindering shunting of electrical current from the at least one electrical terminal to the case that has been induced by electromagnetic interference (EMI) impinging on the medical lead where a frequency of the induced electrical current is above 1 MHz.

7. The AIMD of claim 6, wherein the inductive element is electrically coupled in series between the interior electronic circuitry and one of the at least one electrical terminal and the case.

8. The AIMD of claim 7, wherein the one of the at least one electrical terminal and the case is the at least one electrical terminal.

9. The AIMD of claim 7, wherein the one of the at least one electrical terminal and the ease is the case.

10. The AIMD of claim 6, wherein an operating frequency of the interior electronic circuitry is below 1 KHz.

11. An active implantable medical device (AIMD) for use with a medical lead carrying at least one lead electrode, comprising:
    interior electronic circuitry configured for performing a medical function via the medical lead, wherein the interior electronic circuitry comprises a microcontroller;
    an electrically conductive case containing the interior electronic circuitry;
    a battery disposed within the case;

at least one electrical terminal configured for electrically coupling the interior electronic circuitry respectively to the least one lead electrode;

at least one capacitive element electrically coupled respectively in series between the at least one electrical terminal and a common terminal; and another capacitive element electrically coupled in series between the case and the common terminal, thereby electrically isolating the at least one electrical terminal and case from each other at an operating frequency of the interior electronic circuitry.

12. The AIMD of claim 11, wherein the interior electronic circuitry is configured for conveying electrical stimulation energy between the at least one electrical terminal and the case.

13. The AIMD of claim 11, wherein the interior electronic circuitry is configured for sensing a physiological parameter between the at least one electrical terminal and the case.

14. The AIMD of claim 11, further comprising a connector configured for removably connecting the medical lead to the at least one electrical terminal.

15. The AIMD of claim 11, wherein the operating frequency of the interior electronic circuitry is below 100 KHz.

16. An active implantable medical device (AIMD) for use with a medical lead carrying at least one lead electrode, comprising:

interior electronic circuitry configured for performing a medical function via the medical lead;

an electrically conductive case containing the interior electronic circuitry;

at least one electrical terminal configured for electrically coupling the interior electronic circuitry respectively to the least one lead electrode;

at least one capacitive element electrically coupled respectively in series between the at least one electrical terminal and a common terminal;

another capacitive element electrically coupled in series between the case and common terminal, thereby electrically isolating the at least one electrical terminal and case from each other at an operating frequency; and an inductive element disposed within the case and coupled in series between the at least one electrical terminal and the case, the inductive element being configured for hindering shunting of electrical current from the at least one electrical terminal to the case that has been induced by electromagnetic interference (EMI) impinging on the medical lead where a frequency of the induced electrical current is above 1 MHz.

17. The AIMD of claim 16, wherein the inductive element is electrically coupled in series between the interior electronic circuitry and one of the at least one electrical terminal and the case.

18. The AIMD of claim 17, wherein the one of the at least one electrical terminal and the case is the at least one electrical terminal.

19. The AIMD of claim 17, wherein the one of the at least one electrical terminal and the case is the case.

20. The AIMD of claim 16, wherein the operating frequency of the interior electronic circuitry is below 1 KHz.

* * * * *